US008158609B1

(12) United States Patent
Marsh et al.

(10) Patent No.: US 8,158,609 B1
(45) Date of Patent: Apr. 17, 2012

(54) USE OF CYCLODEXTRINS AS AN ACTIVE INGREDIENT FOR TREATING DRY AMD AND SOLUBILIZING DRUSEN

(75) Inventors: David Allen Marsh, Fort Worth, TX (US); Robert J. Collier, Jr., Arlington, TX (US); Michael A. Kapin, Arlington, TX (US); Youqin Tian, Colleyville, TX (US); Eliot Mark Slovin, Arlington, TX (US)

(73) Assignee: Novartis AG, Basel (CH)

( * ) Notice: Subject to any disclaimer, the term of this patent is extended or adjusted under 35 U.S.C. 154(b) by 566 days.

(21) Appl. No.: 11/934,132

(22) Filed: Nov. 2, 2007

Related U.S. Application Data

(60) Provisional application No. 60/864,059, filed on Nov. 2, 2006.

(51) Int. Cl.
*A61K 31/724* (2006.01)
(52) U.S. Cl. .................................................. 514/58
(58) Field of Classification Search ............. 514/58
See application file for complete search history.

(56) References Cited

U.S. PATENT DOCUMENTS

| | | | |
|---|---|---|---|
| 4,533,637 A | 8/1985 | Yamane et al. | |
| 4,727,064 A | 2/1988 | Pitha | |
| 4,956,351 A * | 9/1990 | Mesens et al. | 514/58 |
| 4,978,532 A | 12/1990 | El-Rashidy | |
| 4,983,586 A | 1/1991 | Bodor | |
| 4,997,652 A | 3/1991 | Wong | |
| 5,024,998 A | 6/1991 | Bodor | |
| 5,120,546 A | 6/1992 | Hansen et al. | |
| 5,185,152 A | 2/1993 | Peyman | |
| 5,288,497 A | 2/1994 | Stanley et al. | |
| 5,288,498 A | 2/1994 | Stanley et al. | |
| 5,376,645 A * | 12/1994 | Stella et al. | 514/58 |
| 5,576,311 A * | 11/1996 | Guy | 514/179 |
| 5,718,922 A | 2/1998 | Herrero-Vanrell et al. | |
| 5,747,544 A | 5/1998 | Garnett et al. | |
| 5,854,015 A | 12/1998 | Garnett et al. | |
| 5,919,813 A | 7/1999 | de Juan, Jr. | |
| 6,028,099 A | 2/2000 | de Juan, Jr. | |
| 7,816,497 B2 * | 10/2010 | Ambati | 530/387.9 |

OTHER PUBLICATIONS

Chopdar, A. et al, BMJ, 2003, 326, 485-488.*
Szejtli, Medicinal Research Reviews, 1994, 1493), 353-386.*
Stern, Drug News and Perspectives, 1989, 2, 410-15.*
Berson, 1993, "Retinitis Pigmentosa", Invest Ophthalmol Vis Sci, 34:1659-1676.
Bressler et al., 1994, "Clinicopathologic Correlation of Drusen and Retinal Pigment Epithelial Abnormalities in Age-Related Macular Degeneration", Retina, 14:130-142.
Cruickshank et al., 1993, "Sunlight and Age-Related Macular Degeneration", Arch Ophthalmol., 111:514-518.
Green and Key, 1977, "Senile Macular Degeneration: A Histopathologic Study", Trans Am Ophthalmol Soc, 75:180-254.
Green et al., 1985, "Pathologic Features of Senile Macular Degeneration", Ophthalmol, 92:615-27.
Green and Enger, 1993, "Age-related Macular Degeneration Histopathologic Studies", Ophthalmol, 100:1519-1535.
Green and Küchle, 1997, "Chapter 11 Histopathologic Studies of Choroidal Neovascularization", In: Yannuzzi, L.A., Flower, R.W., Slakter, J.S. (Eds.) Indocyanine green angiography. St. Louis: Mosby, p. 151-156.
Hageman and Mullins, 1999, "Molecular composition of drusen as related to substructural phenotype", Molecular Vision, 5:28.
Heckenlively, 1987, "RP Cone-Rod Degeneration", Trans Am Ophthalmol Soc, 85:438-470.
Li et al., 1991, "Angiostatic Steroids Potentiated by Sulfated Cyclodextrins Inhibit Corneal Neovascularization", Investigative Ophthalmology & Visual Science, 32(11):2898-2905.
Nickells and Zack, 1996, "Apoptosis in ocular disese: a molecular overview", Ophthalmic Genet, 17:145-65.
Pagon, 1988, "Retinitis Pigmentosa", Survey of Ophthalmology, 33:137-177.
Pruett, 1983, "Retinitis Pigmentosa: Clinical Observations and Correlations", Trans Am Ophthalmol Soc, 81:693-735.
Schneider et al., 1998, "Photocoagulation of Well-Defined Choroidal Neovascularization in Age-Related Macular Degeneration", Retina, 18:242-250.
Taylor et al,. 1992, "Long-term Effects of Visible Light on the Eye", Ophthalmol., 110:99-104.
Young, 1988, "Solar Radiation and Age-related Macular Degeneration", 32(4):252-269.

* cited by examiner

*Primary Examiner* — Shaojia Anna Jiang
*Assistant Examiner* — Ganapathy Krishnan
(74) *Attorney, Agent, or Firm* — Teresa J. Schultz

(57) ABSTRACT

The present invention is directed to the treatment of disorders involving the accumulation of drusen, such as dry age-related macular degeneration and geographic atrophy via administration of therapeutically effective amounts of at least one monomeric or polymeric cyclodextrin.

4 Claims, 1 Drawing Sheet

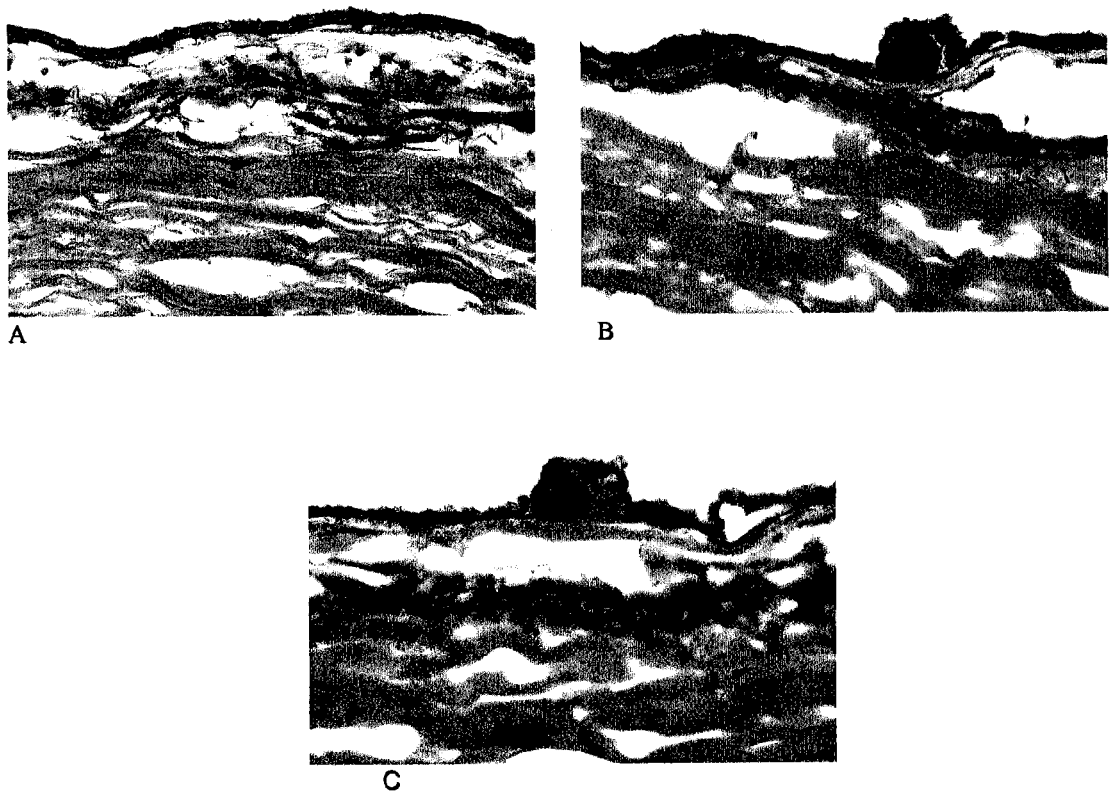

USE OF CYCLODEXTRINS AS AN ACTIVE INGREDIENT FOR TREATING DRY AMD AND SOLUBILIZING DRUSEN

This application claims priority from U.S. Ser. No. 60/864,059 filed Nov. 2, 2006.

BACKGROUND OF THE INVENTION

1. Field of the Invention

The present invention relates to the field of retinal disorders. More specifically, the invention relates to the treatment of disorders involving the accumulation of drusen, such as dry age-related macular degeneration.

2. Description of the Related Art

Age-related macular degeneration (AMD) is the leading cause of blindness in the elderly, with an incidence of about 20% in adults 65 years of age increasing to 37% in individuals 75 years or older. Non-exudative (dry) AMD is characterized by drusen accumulation and atrophy of rod and cone photoreceptors in the outer retina, retinal pigment epithelium (RPE), Bruch's membrane and choriocapillaris; while exudative AMD leads to choroidal neovascularization (Green and Enger, *Ophthalmol*, 100:1519-35, 1993; Green et al., *Ophthalmol*, 92:615-27, 1985; Green and Key, *Trans Am Ophthalmol Soc*, 75:180-254, 1977; Bressler et al., *Retina*, 14:130-42, 1994; Schneider et al., *Retina*, 18:242-50, 1998; Green and Kuchle (1997). In: Yannuzzi, L. A., Flower, R. W., Slakter, J. S. (Eds.) *Indocyanine green angiography*. St. Louis: Mosby, p. 151-6). Retinitis pigmentosa (RP) represents a group of hereditary dystrophies characterized by rod degeneration with secondary atrophy of cone photoreceptors and underlying pigment epithelium. (Pruett, *Trans Am Ophthalmol Soc*, 81:693-735, 1983; Heckenlively, *Trans Am Ophthalmol Soc*, 85:438-470, 1987; Pagon, *Sur Ophthalmol*, 33:137-177, 1988; Berson, *Invest Ophthalmol Vis Sci*, 34:1659-1676, 1993; Nickells and Zack, *Ophthalmic Genet*, 17:145-65, 1996). The pathogenesis of retinal degenerative diseases, such as AMD and RP, is multifaceted and can be triggered by environmental factors in normal individuals or in those who are genetically predisposed. To date more than 100 genes have been mapped or cloned that may be associated with various outer retinal degenerations.

Early stages of macular degeneration are typically treated by combinations of antioxidants or anti-inflammatory agents whose efficacy has not been demonstrated in the clinic. Advanced stages of macular degeneration that lead to severe vision loss are treated either by surgical removal of membranes from the subretinal space, laser photocoagulation, photodynamic therapy, and most recently with VEGF blockers in patients with exudative AMD. No approved treatments are available for the advanced form of dry AMD known as Geographic Atrophy. Laser treatment is also used in the treatment of diabetic retinopathy. It is important to note that both laser photocoagulation of the retina and surgical excision of subretinal membranes or intravitreal membranes results in the destruction of viable retinal neurons.

One obstacle to obtaining regulatory approval for the marketing of treatments for retinal disorders is the lengthy clinical trials that are required. Although inhibition and/or reversion of angiogenesis and/or neovascularization can be illustrated in animal models where the animals are sacrificed and their eye tissues analyzed, it is difficult to determine whether angiogenesis or neovascularization has been effectively halted or reversed in the eyes of live patients. Therefore, in order to establish effectiveness of inhibitors of angiogenesis or neovascularization, for example, it is necessary to show an improvement in visual acuity, which often takes one to two years to manifest meaningfully.

Drusen deposits have been shown to be a significant risk factor for the development of dry AMD. In fact, the underlying cause of dry AMD is thought to be related to drusen deposits. Dry AMD leads to wet AMD or geographic atrophy in approximately 10%-15% of the patient population. Geographic atrophy is characterized by classic lesions in dry AMD. The lesions that lead to geographic atrophy are known as drusen. Drusen deposits are known to be composed of proteins and lipids (i.e., phospholipids, neutral lipids, cerebrosides, gangliosides, numerous other proteins, etc) that are derived from systemic, choriocapillaries and retinal sources. There is currently no approved treatment for halting or reversing loss of vision resulting from dry AMD or geographic atrophy.

Cyclodextrins have long been known to be superb solubilizing agents through their ability to complex with lipophilic materials and some proteins to form inclusion complexes. For example, (1) U.S. Pat. No. 4,533,637 discusses the use of cyclodextrins to make inclusion complexes with lipophilic materials (lipids) to make a low-serum culture media; (2) U.S. Pat. No. 4,727,064 discusses the use of cyclodextrins to solubilize drugs in inclusion complexes; and (3) U.S. Pat. Nos. 4,983,586 and 5,024,998 discuss the use of cyclodextrins (in concentrations of 20-50%) to solubilize (as inclusion complexes) lipophilic drugs for injection. None of these references discuss the delivery of therapeutic amounts of cyclodextrins into the subTenons area of the eye, in the absence of inclusion complexes.

Cyclodextrins have been increasingly used in pharmaceutical formulations, in low concentrations, as a solubilizing or penetrating agent. For example, U.S. Pat. Nos. 5,919,813 and 6,028,099 (de Juan et al.) are directed to the treatment of diabetic retinopathy or choroidal neovascularization via administration of protein tyrosine kinase inhibitors, such as genistein or derivatives thereof. In describing the pharmaceutical compositions for use in the claimed treatment methods, the applicants state that the PTK inhibitor can be formulated as cyclodextrin inclusion complexes, among other types of suggested excipients for pharmaceutical formulations. These patents do not suggest the use of cyclodextrins in therapeutically effective amounts as active ingredients for the solubilization of drusen or the treatment of dry AMD.

U.S. Pat. Nos. 5,747,544 and 5,854,015 (Garnett et al.) describe a method for preparing pure stereoisomers of zeaxanthin and their use in the treatment of AMD. The specification explains that it may be desirable to administer the zeaxanthin formulations via injection in some patients, which can be carried out using implants or injectable carrier liquids. In the discussion, it is stated that "carrier formulations that are used for injection of hydrophobic compounds typically include water, a buffering agent, and an organic compound having a plurality of hydroxyl groups, such as propylene glycol or dextran or cyclodextrin compounds." Again, the cyclodextrin is clearly used as an excipient in these types of carrier formulations. It is not contemplated that cyclodextrin itself could be administered in therapeutically effective amounts as an active ingredient for the solubilization of drusen or the treatment of dry AMD.

Li et al. (IOVS, 32(11):2898-2905 (1991)) showed that topical applications of a composition containing sulfated cyclodextrins with angiostatic steroids enhance the ability of the angiostatic corticosteroids to inhibit angiogenesis. In these compositions, the cyclodextrins were used as excipients and were not present in therapeutically effective amounts.

All of the therapies described above utilize cyclodextrins solely as an excipient in pharmaceutical formulations containing other types of small molecule active ingredients for the treatment of AMD. None of the publications discussed suggest the use of cyclodextrins in therapeutically effective amounts as an active ingredient for the solubilization of drusen and/or the treatment of dry AMD. Furthermore, measurement of effectiveness of those therapies often requires lengthy clinical trials in order to determine whether visual acuity has been improved.

What is needed is a therapy for dry AMD that targets the large, soft drusen that accumulate in the eyes of patients suffering from, or at risk for developing, dry AMD. Moreover, it is desirable to be able to discern quickly, i.e., within a matter of weeks or months, rather than years, whether such a therapy is effectively eliminating such drusen deposits, thereby decreasing the risk of vision loss due to dry AMD.

SUMMARY OF THE INVENTION

The present invention overcomes these and other drawbacks of the prior art by providing compositions containing therapeutically effective amounts of at least one monomeric or polymeric cyclodextrin for solubilizing drusen and/or treating dry AMD in a patient suffering from, or at risk for developing, such disorder. The present invention further provides methods for solubilizing drusen and/or treating dry AMD in patients suffering therefrom or at risk for developing such disorder due to deposits of drusen, via administration of such a composition.

BRIEF DESCRIPTION OF THE DRAWINGS

The following drawing forms part of the present specification and is included to further demonstrate certain aspects of the present invention. The invention may be better understood by reference to this drawing in combination with the detailed description of specific embodiments presented herein.

FIG. 1A, FIG. 1B, FIG. 1C-FIG. 1A: illustrates intact RPE attached to Bruch's Membrane. H&E 40× FIG. 1B: shows a drusen between RPE and Bruch's membrane with non treatment. H&E 40× FIG. 1C: shows the reduced size of a drusen after treating w/25% Hydroxypropyl β-cyclodextrin for 2 hours. H&E 40×

DETAILED DESCRIPTION PREFERRED EMBODIMENTS

Retinal diseases are often disruptive to the tissue and can result in a loss of visual function for millions of patients. For example, retinal tissues can be damaged by environmental factors, such as light exposure, which is known to contribute to the progression of retinal degenerative disorders such as AMD (Young 1988; Taylor et al. 1992; Cruickshank et al. 1993). To date, no effective treatment exists for neurodegenerative disorders of the retina. Early stages of macular degeneration are typically treated by combinations of antioxidants or anti-inflammatory agents whose efficacy has not been demonstrated in the clinic. Advanced stages of macular degeneration that lead to severe vision loss are treated either by surgical removal of membranes from the subretinal space, laser photocoagulation, photodynamic therapy, and most recently with VEGF blockers in patients with exudative AMD. No approved treatments are available for the advanced form of dry AMD known as Geographic Atrophy. Laser treatment is also used in the treatment of diabetic retinopathy. It is important to note that both laser photocoagulation of the retina and surgical excision of subretinal membranes or intravitreal membranes results in the destruction of viable retinal neurons.

Studies have shown that drusen form as extracellular deposits between the retinal pigment epithelium (RPE) basal lamina and the inner collagenous layer of Bruch's membrane. They cause lateral stretching of the RPE monolayer and physical displacement of the RPE from its immediate vascular supply, the choriocapillaris. This displacement likely creates a physical barrier that may impede normal metabolite and waste diffusion between the choriocapillaris and the neural retina. In this paradigm, wastes may be concentrated near the RPE and the diffusion of oxygen, glucose, and other nutritive or regulatory serum-associated molecules required to maintain the health of the outer retina and RPE are inhibited. It has also been suggested that drusen perturb photoreceptor cell function by placing pressure on rods and cones and/or by distorting photoreceptor cell alignment (Hageman and Mullins, Molec. Vis. 5:28 (1999)).

The present inventors have discovered, for the first time, that monomeric or polymeric cyclodextrins, when administered in therapeutically effective amounts, can solubilize drusen, thereby inhibiting or preventing vision loss associated with dry AMD resulting from the accumulation of drusen. Moreover, solubilization of drusen via administration of therapeutically effective amounts of at least one monomeric or polymeric cyclodextrin can improve visual acuity in patients suffering from or at risk for developing dry AMD.

Cyclodextrins are known to be effective solubilizing agents through their ability to complex with lipophilic materials and some proteins to form inclusion complexes. They have been utilized as a solubilizing agent or penetration-enhancing agent in pharmaceutical formulations for a number of years. For example, U.S. Pat. Nos. 4,978,532; 5,120,546; 5,288,497; and 5,288,498 discuss the use of cyclodextrins as a solubilizing agent or penetration-enhancing agent. The amounts of cyclodextrins used for these purposes are below the therapeutically effective amounts used with the methods of the present invention.

As used herein, the phrase "therapeutically effective amount" refers to concentrations of monomeric or polymeric cyclodextrins within the compositions of the invention that are effective for eliciting a therapeutic response in a patient, e.g., the solubilization of drusen such that the damaging effects of its accumulation are avoided or ameliorated. Therapeutically effective amounts of the monomeric or polymeric cyclodextrin compounds for use in the compositions of the invention will be higher than the concentrations of such compounds in pharmaceutical formulations when present as an excipient for a different active ingredient. In the present case, monomeric or polymeric cyclodextrins are present in amounts high enough for such compounds to be considered an active ingredient themselves.

The compositions of the invention may further include an additional active agent, such as a neuroprotective compound, an anti-angiogenic compound, or a neovascularization inhibiting compound. Anti-angiogenic compounds for use in the compositions and methods of the present invention may include anecortave acetate. Neovascularization inhibiting compounds for use in the compositions and methods of the present invention may include ranibizumab, bevacizumab, other VEGF inhibitors, and receptor tyrosine kinase inhibitors. Other compounds that could be useful in combination with the compositions of the present invention include anti-inflammatory agents (e.g., steroidal and non-steroidal agents); tyrosine kinase inhibitors; anti-infectives, (e.g., antibiotics, antivirals, and antifungals); antiallergic agents (e.g., antihistamines and mast cell stabilizers); cyclooxygenase inhibitors, (e.g., Cox I and Cox II inhibitors); combinations of anti-infective and anti-inflammatory agents; decongestants; anti-glaucoma agents, (e.g., adrenergics, β-adrenergic blocking agents, α-adrenergic agonists, parasympathomimetic agents, cholinesterase inhibitors, carbonic anhydrase inhibitors, and prostaglandin analogs, and combinations of such anti-glaucoma agents); antioxidants; nutritional supplements; drugs for the treatment of cystoid macular edema (e.g., non-steroidal anti-inflammatory agents); drugs for the treatment of ARMD, (e.g., angiogenesis inhibitors and nutritional supplements); drugs for the treatment of herpetic infections and CMV ocular infections; drugs for the treatment of proliferative vitreoretinopathy (e.g., antimetabolites and fibrinolytics); wound modulating agents (e.g., growth factors); antimetabolites; and neuroprotective drugs (e.g., eliprodil). It is further contemplated that the compositions of the present invention may be used in conjunction with photodynamic therapy.

Although the compositions of the invention may include an additional active agent, as described herein, it is also contemplated that the compositions of the invention may be administered in conjunction with additional active agents for treating retinal disorders where the additional active agents are administered in separate compositions either concurrently with administration of the compositions of the invention, prior to their administration or subsequent to their administration. For example, the compositions of the invention could be administered minutes, hours, days, or weeks prior to or subsequent to administration with an additional active agent for treating retinal disorders. In preferred embodiments, the compositions of the invention will be administered with the additional active agent during the same office visit. Alternatively, the compositions of the invention could be administered to a patient from one day to a month or two months prior to administration of the additional active agent.

When used in conjunction with additional active agents for the treatment of AMD or other retinal disorders, the compounds of the invention function to physiochemically solubilize the drusen present in the patient's eye, shrinking the size of such drusen, or eliminating them altogether, within a matter of days or weeks, so that the additional active agent can provide longer lasting neuroprotection and/or inhibition of angiogenesis or neovascularization, thereby stabilizing or improving the patient's vision. In some aspects of the invention, the therapeutically effective amount of the cyclodextrin and the additional active agent are present in the same composition. In this case, a low concentration of a cyclodextrin may be incorporated in the composition in order to solubilize or act as a penetration-enhancer for the additional active agent. The additional active agent may be incorporated as an inclusion complex with the cyclodextrin, which will help carry the additional active agent to the active site. In such compositions, a separate, therapeutically effective amount of at least one monomeric or polymeric cyclodextrin is present in the composition. The therapeutically effective amount of the monomeric or polymeric cyclodextrin is not part of an inclusion complex. The monomeric or polymeric cyclodextrin that is present in a therapeutically effective amount may be the same cyclodextrin, or a different cyclodextrin, from the cyclodextrin that is acting to solubilize the additional active agent.

The compositions of the invention will generally be administered locally, to the eyes of patients suffering from dry AMD or at risk for developing dry AMD due to the accumulation of drusen. Local administration includes intravitreal, topical ocular, transdermal patch, subdermal, parenteral, intraocular, subconjunctival, or retrobulbar or subtenon's injection, trans scleral (including iontophoresis), posterior juxtascleral delivery, or slow release biodegradable polymers or liposomes. The compounds can also be delivered in ocular irrigating solutions. Concentrations should range from about 0.001 μM to about 100 μM, preferably about 0.01 μM to about 5 μM.

The compounds can be incorporated into various types of ophthalmic formulations for delivery to the eye (e.g., topically, intracamerally, juxtasclerally, or via an implant). They may be combined with ophthalmologically acceptable preservatives, surfactants, viscosity enhancers, gelling agents, penetration enhancers, buffers, sodium chloride, and water to form aqueous, sterile ophthalmic suspensions or solutions or preformed gels or gels formed in situ. Ophthalmic solution formulations may be prepared by dissolving the compound in a physiologically acceptable isotonic aqueous buffer. Further, the ophthalmic solution may include an ophthalmologically acceptable surfactant to assist in dissolving the compound. The ophthalmic solutions may contain a viscosity enhancer, such as, hydroxymethylcellulose, hydroxyethylcellulose, hydroxypropylmethylcellulose, methylcellulose, polyvinylpyrrolidone, or the like, to improve the retention of the formulation in the conjunctival sac. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940, or the like, according to the published formulations for analogous ophthalmic preparations; preservatives and tonicity agents can be incorporated.

If dosed topically, the compounds are preferably formulated as topical ophthalmic suspensions or solutions, with a pH of about 4 to 8. The compounds will normally be contained in these formulations in an amount 0.001% to 5% by weight, but preferably in an amount of 0.01% to 2% by weight. Thus, for topical presentation, 1 to 2 drops of these formulations would be delivered to the surface of the eye 1 to 4 times per day according to the discretion of a skilled clinician.

In preferred aspects, the compositions of the invention, containing therapeutically effective amounts of at least one monomeric or polymeric cyclodextrins, are delivered intravitreally either through an injection (perhaps microspheres), an intravitreal device, or placed in the sub-Tenon space by injection, gel, or implant, or by other methods discussed above.

If delivered as a solution, the therapeutically effective amount of cyclodextrin in the composition might be about 18-44 μM, of a concentration of about 20-50%. If formulated as a suspension, a therapeutically effective amount of cyclodextrin is preferably about 20-80%. In another embodiment, the therapeutically effective amount of cyclodextrin is administered in the form of a mini-tablet, each weighing from about 1 mg to about 40 mg, preferably about 5 mg. From one to twenty such mini-tablets are injected [dry] into the sub-Tenon space through a trochar in one dose, so that a total single dose of 50-100 mg [44-88 μM] is injected.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Unfixed 90-year-old, female, donor eye with AMD drusen was immersed in 30% sucrose in PBS buffer at pH 7.4 for 24 hours at 4° C. for cryoprotection, then embedded in OCT. For cryostat sections, the eye was serially sectioned at 8 μm thickness and stored at −70° C. Drusen were identified under the microscope. Unfixed fresh frozen mouse brown fat tissue was sectioned at 10 μm thickness as the positive control.

Cyclodextrin solutions were made as set forth in Table 1

TABLE 1

| | | | | | | |
|---|---|---|---|---|---|---|
| 10% α-cyclodextrin | 15' | 30' | 1 h | 2 h | 4 h | 15 h |
| 1.75% β-cyclodextrin | 15' | 30' | 1 h | 2 h | 4 h | 15 h |
| 20% γ-cyclodextrin | 15' | 30' | 1 h | 2 h | 4 h | 15 h |
| 25% Hydroxypropyl β-cyclodextrin | 15' | 30' | 1 h | 2 h | 4 h | 15 h |

Hydroxypropyl β-cyclodextrin selected compound was titered to the best concentration by mouse fat tissue at 37° C. for 24 hrs (Table.2).

TABLE 2

| |
|---|
| 25% Hydroxypropyl β-cyclodextrin |
| 35% Hydroxypropyl β-cyclodextrin |
| 45% Hydroxypropyl β-cyclodextrin |
| 30% Sulfonyletherbutyl β-cyclodextrin |

A viable in vitro assay to evaluate compounds with a potential to remove drusen in the eye was explored. Sections with drusen were treated with cyclodextrin for 30 min, 1 hr, 2 hrs, 4 hrs, 15 hrs at room temperature. In a subsequent experiment, sections with drusen were immersed in 40 ml of 25% Hydroxypropyl β-cyclodextrin at 37° C. for 24 hrs.

Histochemistry: untreated control drusen section and treated frozen drusen section were post-fixed with 4% Paraformaldehyde for 20 min and stained with routing Hemotoxylin and Eosin (H&E) with Leica Autostainer XL, Program #4 (Frozen section H&E) for demonstration of drusen. Oil Red O (ORO) staining was designed for demonstration of potential lipids in drusen. Unfixed frozen human eye drusens were considered closest to the in vivo state of drusen. Mouse brown fat was used for positive control.

Results:

Histopathologically, eosinophilic drusen appeared between the basement membrane of the RPE by H&E staining. Drusen shows no change after treating the section with compounds on different time course at RT by H&E staining (Tab.1; FIG. 1A, B, C).

Drusen shows no change after treating the section with 40 ml of different concentration selected Hydroxypropyl β-cyclodextrin at 37° C. for 24 hrs by H&E staining which indicated the Hydroxypropyl β-cyclodextrin is not able to dissolve the solid drusen in this experimental condition.

Lipid histochemistry of fresh fat tissue: Mouse brown fat was used as the positive control tissue staining with Oil Red O (ORO staining), a special staining to detect neutral lipid. The 25%-45% Hydroxypropyl β-cyclodextrin has effect on dissolving the partial fat tissue at 37° C. for 24 hrs.

Lipid histochemistry of drusen in eyes with AMD: Drusen were stained positively with ORO staining, which indicated lipids were presented in drusen and those lipid-containing drusen were stained negatively with ORO staining after being treated with 40 ml of 25% Hydroxypropyl β-cyclodextrin at 37° C. for 24 hrs which showed the 25% Hydroxypropyl β-cyclodextrin efficacy in dissolving the lipid component of drusen.

Summary:

25% Hydroxypropyl β-cyclodextrin has efficacy in dissolving fresh mouse fat tissue. Compare with untreated fat tissue, the partial fat tissues were dissolved in the 25%-45% Hydroxypropyl β-cyclodextrin and 30% Sulfonyletherbutyl β-cyclodextrin at 37° C. for 24 hrs.

25% Hydroxypropyl β-cyclodextrin could not completely dissolve drusen which contained multi-components like lipid, cholesterol, β-amyloid, activated complement components and other drusen-associated proteins (H&E stain). However our study first demonstrated the 25% Hydroxypropyl β-cyclodextrin has efficacy in dissolving the lipid component of drusen (ORO stain).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

All references cited herein, to the extent that they provide exemplary procedural or other details supplementary to those set forth herein, are specifically incorporated herein by reference.

We claim:

1. A method for shrinking the size of drusen in the eye of a patient suffering from dry age-related macular degeneration by solubilizing the lipid component of said drusen, said method comprising administering to a patient in need thereof, a composition comprising from 20% to 80% by weight of at least one cyclodextrin selected from the group consisting of hydroxypropyl β-cyclodextrin, sulfonyletherbutyl β-cyclodextrin, and a polymer of β-cyclodextrin, wherein the composition is administered via intravitreal injection, and wherein the lipid component of said drusen is solubilized within the cyclodextrin thereby shrinking the size of said drusen.

2. The method of claim 1, wherein the amount of cyclodextrin in the composition is from 20% to 50% by weight.

3. The method of claim 1, wherein the concentration of cyclodextrin in the composition is from about 40 μM to about 100 μM.

4. A method for solubilizing the lipid component of drusen in the eye of a patient suffering from dry age-related macular degeneration, said method comprising administering to said patient, a composition comprising from 20% to 80% by weight of at least one cyclodextrin selected from the group consisting of hydroxypropyl β-cyclodextrin, sulfonyletherbutyl β-cyclodextrin, and a polymer of β-cyclodextrin, wherein the composition is administered via intravitreal injection.

* * * * *